United States Patent [19]
Herber et al.

[11] 3,969,254
[45] July 13, 1976

[54] CHEMICAL COMPOUNDS

[75] Inventors: John F. Herber, St. Louis; Robert W. Street; William R. Richard, Jr., both of Kirkwood, all of Mo.

[73] Assignee: Monsanto Company, St. Louis, Mo.

[22] Filed: Sept. 23, 1975

[21] Appl. No.: 615,950

Related U.S. Application Data

[63] Continuation-in-part of Ser. No. 454,649, March 25, 1974, abandoned.

[52] U.S. Cl. .................................. 252/78; 252/49.8; 252/49.9; 252/56 S; 252/79; 260/346.2 R; 260/347.5; 260/347.8
[51] Int. Cl.² .................. C10M 3/40; C10M 3/20; C07D 307/12
[58] Field of Search .................. 260/346.2 R, 347.5, 260/347.8, 346.2 M; 252/78, 79, 49.8, 49.9, 56 S

[56] References Cited
OTHER PUBLICATIONS

Yu et al., Chem. Abs. vol. 55, col. 24711 (1961).
Befirov et al., Chem. Abs., vol. 64, col. 15865–15866 (1966).
Befirov et al., Chem. Abs., vol. 62, col. 14643–14644 (1965).
Befirov et al., Chem. Abs., vol. 69, item 27283 (1968).
Kunstmann et al., J. Am. Chem. Soc., vol. 84, pp. 4115–4125 (1962).

*Primary Examiner*—Harris A. Pitlick
*Attorney, Agent, or Firm*—William C. Gerstenzang

[57] ABSTRACT

A new class of monoepoxyendooxycyclohexyl compounds useful as acid scavengers and corrosion inhibitors in functional fluid compositions.

15 Claims, No Drawings

CHEMICAL COMPOUNDS

This application is a continuation in part of copending application Ser. No. 454,649, filed Mar. 25, 1974 and now abandoned.

FIELD OF THE INVENTION

This invention relates to a new class of monoepoxyendooxycyclohexyl compounds and to functional fluid compositions, particularly hydraulic fluids, containing such compounds to inhibit acid buildup.

DESCRIPTION OF THE PRIOR ART

Functional fluids have been utilized in many different types of applications such as electronic coolants, diffusion pump fluids, lubricants, damping fluids, bases for greases, power transmission and hydraulic fluids, heat transfer fluids, heat pump fluids, refrigeration equipment fluids and as filter mediums for air-conditioning systems. Of these uses, hydraulic fluids intended for use in the hydraulic system of aircraft for operating various mechanisms and aircraft control systems must meet stringent functional and use requirements. One of the most important requirements for an aircraft hydraulic fluid is that the fluid be chemically stable to resist oxidative and thermal degradation which can result in the formation of acid and the corrosive attack of metals in contact with the hydraulic fluid.

In order the control the degree of acid buildup during use of the fluid and inhibit corrosion of the components in the hydraulic system, it is conventional to add certain acid scavengers and/or corrosion inhibitors to the hydraulic fluid base stock.

Although a variety of compounds have been suggested for use as corrosion inhibitors, acid acceptors which act as proton acceptors and prevent the buildup of corrosive acids in the fluids when they undergo decomposition under prolonged use at high temperatures are generally preferred. A particularly preferred class of such materials comprises epoxy compounds, especially epoxidized naturally occurring material such as epoxidized unsaturated glycerides including epoxidized soybean oil, epoxidized castor oil, epoxidized linseed oil, epoxidized fats and the like. Other suggested materials include epoxy esters such as butylepoxyacetoxystearate, glyceryl triepoxyacetoxystearate, isooctylepoxystearate, epoxidized isooctyl phthalate and the like. Also suggested are various alkyl and arylalkyl epoxides such as epoxy decane, epoxy hexadecane, epoxy octadecane, epoxy cyclododecane, and the like, and glyceryl and various glycidyl ethers such as phenyl glycidyl ether, glycidyl cyclohexyl ether, alkyl glycidyl ether, and the like.

More recently it has been suggested that a particular class of epoxy compounds, the 3,4-epoxycycloalkyl-3,4-epoxycycloalkyl carboxylates, are particularly useful as acid acceptors for hydraulic fluids and are more effective than the epoxy compounds used heretofore. A particularly preferred compound is 3,4-epoxycyclohexylmethyl-3,4-epoxycyclohexane carboxylate. These compounds are well known chemical entities which have been used as acid scavengers for chlorinated diphenyl dielectric fluids prior to their introduction as inhibitors for hydraulic fluids.

Although 3,4-epoxycycloalkyl-3,4-epoxycycloalkyl carboxylates are effective acid scavengers for common hydraulic fluid compositions, they have a disadvantage in that they may cause resinous deposits to form around the fluid pump shaft at the point of seal. The formation of deposits is of particular concern in aircraft hydraulic systems which operate under pressure and where the deposits soon result in fluid leakage through the seal. Although the problem of shaft seal leakage is not serious from an aircraft operational point of view, it represents a sufficient nuisance that the aircraft industry and aircraft hydraulic fluid manufacturers have actively sought alternative acid acceptors which are as effective and efficient as the 3,4-epoxycyclohexylmethyl-3,4-epoxycyclohexane carboxylate but which do not have the deposit and leakage problem associated with this material.

It is accordingly an object of this invention to provide an acid acceptor effective to prevent acid buildup in functional fluid compositions. Another object of this invention is to provide an acid acceptor which can be used without adverse secondary effects in functional fluids which may also contain a polymeric V.I. improver. A further object of this invention is to provide functional fluid compositions which are resistant to thermal and oxidative degradation and which are suitable for use in aircraft hydraulic systems. It is a yet further object of this invention to provide an aircraft hydraulic fluid containing a polymeric V.I. improver and an epoxide acid acceptor which does not cause pump shaft seal leakage. Yet further objects will be apparent from the following description of the invention.

SUMMARY

In accordance with this invention, it was surprisingly found that compounds represented by the following formula effectively prevent acid buildup in functional fluid compositions:

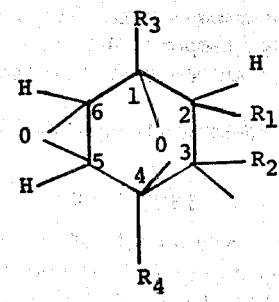

FORMULA I wherein $R_1$ is $-(CH_2)_{0-3}-C(O)OR$, $-C(O)R$, or $-CH_2OR$ wherein R is an alkyl radical having from 1 to about 18 carbon atoms, $R_2$ is $R_1$, hydrogen or an alkyl radical having from 1 to about 9 carbon atoms, $R_3$ and $R_4$ are individually hydrogen or an alkyl radical having from 1 to 4 carbon atoms. Preferably, R has 1 to 12 carbon atoms.

Preferred compounds that can be employed in the practice of the present invention are those represented by the following structure

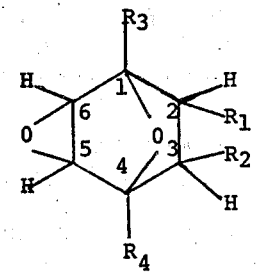

FORMULA IA wherein $R_1$ is $-(CH_2)_{0-3}-C(O)R, -C(O)R,$ or $CH_2OR$ wherein R is an alkyl radical having from 1 to about 18 carbon atoms, $R_2$ is $R_1$, hydrogen or an alkyl radical having from 1 to 9 carbon atoms and $R_3$ and $R_4$ are individually hydrogen or an alkyl radical having from 1 to 4 carbon atoms; when $R_1$ is $-(CH_2)_0-C(O)OR$ $R_2$ is not H or $-(CH_2)_0-C(O)OR$.

DESCRIPTION OF THE PREFERRED EMBODIMENTS

Representative compounds of this invention include the following:

DIESTERS

Diethyl 5,6-epoxy-1,4-endooxycyclohexane-2,3-dicarboxylate,
dihexyl 5,6-epoxy-1,4-endooxycyclohexane-2,3-dicarboxylate,
diheptadecyl 5,6-epoxy-1,4-endooxycyclohexane-2,3-dicarboxylate,
butylmethyl 5,6-epoxy-1,4-endooxycyclohexane-2,3-dicarboxylate
didecyl 5,6-epoxy-1-ethyl-1,4-endooxycyclohexane-2,3-dicarboxylate,
didodecyl 5,6-epoxy-1-methyl-4-butyl-1,4-endooxycyclohexane 2,3-dicarboxylate,
ditetradecyl 5,6-epoxy-1,4-endooxycyclohexylene-2,3-di-(α-acetate)
di(2ethyl-hexyl)5,6-epoxy-1,4-endooxycyclohexylene-2,3-di-(β-propanoate)

ETHERS 2-methoxy 5,6-epoxy-1,4-endooxycyclohexane
2-hexoxy 5,6-epoxy-1,4-endooxycyclohexane
2-decoxy 5,6-epoxy-1,4-endooxycyclohexane
2-octadecoxy 5,6-epoxy-1,4-endooxycyclohexane
2-ethoxy 5,6-epoxy-1-methyl-1,4-endooxycyclohexane
2-nonoxy 5,6-epoxy-4-ethyl-1,4-endooxycyclohexane

DIETHERS 2,3-diethoxy-5,6-epoxy-1,4 endooxycyclohexane
2,3-diheptoxy-5,6-epoxy-1,4 endooxycyclohexane
2,3-didodecoxy-5,6-epoxy-1,4 endooxycyclohexane
2,3-dipentoxy-5,6-epoxy-4 butyl-1,4 endooxycyclohexane
2,3-dioctoxy-5,6-epoxy-1-methyl-4-butyl-1,4-endooxycyclohexane

KETONES propyl 5,6-epoxy-1,4-endooxycyclohexyl ketone
2-ethylhexyl-5,6-epoxy-1,4-endooxycyclohexyl ketone
pentadecyl-5,6-epoxy-1,4-endooxycyclohexyl ketone
octadecyl-5,6-epoxy-1-propyl-1,4-endooxycyclohexyl ketone
nonyl-5,6-epoxy-4-butyl-1,4-endooxycyclohexyl ketone

DIKETONES dibutyl 2,3(5,6-epoxy-1,4-endooxycyclohexylene) diketone
dihexadecyl 2,3(5,6-epoxy-1,4-endooxycyclohexylene) diketone
diethyl 2,3(5,6-epoxy-1,4-endooxycyclohexylene) diketone
didodecyl 2,3(5,6-epoxy-1-methyl-1,4-endooxycyclhexylene) diketone Particularly preferred epoxy compounds that can be employed in the practice of the present invention are those represented by the following structure:

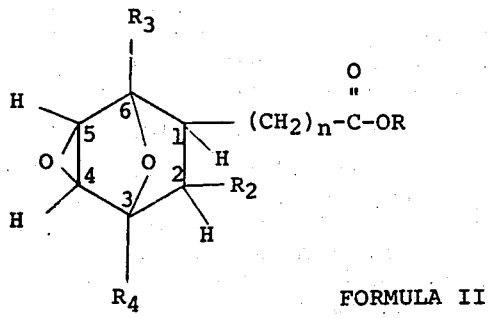

FORMULA II wherein $R_2$ is hydrogen or an alkyl of from 1 to 9 carbon atoms, $R_3$ and $R_4$ are individually hydrogen or an alkyl of from 1 to 4 carbon atoms, R is an alkyl of from 1 to 18 carbon atoms and n is an integer of from 0 to 3. Preferably, R is an alkyl from 1 to 9 carbon atoms, $R_2$, $R_3$ and $R_4$ are hydrogen and $n$ is 0. Representative examples of this class of compounds include methyl 5,6-epoxy-1,4-endooxycyclohexane-2-carboxylate, decyl 5,6-epoxy-1,4-endooxycyclohexane-2-carboxylate, heptadecyl 5,6-epoxy-1,4-endooxycyclohexane-2-carboxylate, ethyl-5,6-epoxy-1-ethyl-1,4-endooxycyclohexane-2-methylenecarboxylate, 2-ethylhexyl-5,6-epoxy-1,4-endooxycyclohexane-2-carboxylate, methyl 5,6-epoxy-1,4-endooxycyclohexyl-β-propanoate.

These compounds may be prepared by those procedures well known in the art, for example, those procedures described in U.S. Pat. No. 3,187,018 the subject matter of which is incorporated herein by reference.

The epoxy esters of this invention may be prepared by first reacting furan with an alkyl acrylate. The reaction product is converted to the epoxy esters of this invention by oxidizing the olefinic linkage contained in the reaction product. Peracetic acid is particularly well suited for this reaction, since it may be carried out under relatively mild conditions and with a minimum of operating difficulty.

The diesters of this invention may be prepared by first reacting furan with maleic anhydride and then reacting this reaction product with an appropriate alcohol. Epoxidation is achieved by oxidizing the olefinic linkage with peracetic acid.

Epoxy mono ethers of this invention are prepared in the same manner as epoxy mono esters except an alkyl vinyl ether is used in place of the alkyl acrylate. Diethers are prepared by using acetylene glycol dialkyl ethers.

Epoxy ketones of this invention are prepared by using alkyl vinyl ketones or 1,4-dialkyl-1,4-diketobutene-2 in place of the alkyl acrylate used to prepare the epoxy mono esters.

Functional fluid compositions of this invention comprise a major amount of at least about 50 percent by weight of a base stock material selected from the group consisting of esters or amides of an acid of phosphorus, di- or tricarboxylic acid esters, esters of polyhydric compounds and mixtures thereof, from 0 to minor amounts of one of more other base stock materials or base stock modifiers, and from about 0.1 to 10 percent by weight of one of the above mentioned compounds. The compositions may include polymeric V. I. improvers and other conventional additives and are particularly useful as aircraft hydraulic fluids.

The concentration of the epoxy compound in the functional fluid is adjusted according to the demands of the system and nature of the base stock being employed in order to provide compositions which contain sufficient amounts of epoxy material to inhibit acid buildup during normal operation. It has been found that the concentration of epoxy compound required to inhibit and control acid buildup in a particular base stock varies according to the composition of the base stock or blends of base stocks. It has generally been found that preferred additive levels of epoxy compounds are from 0.10 weight percent to 5.0 weight percent, although concentrations of 10 percent or higher are also effective and may be used. Thus, included in the present invention are functional fluid compositions comprising a base stock material and any of the epoxy compounds represented by Formula I in a concentration sufficient to control and inhibit acid buildup in the base stock.

The fluid compositions of this invention can be compounded in any manner known to those skilled in the art for incorporating an additive into a base stock, as for example by adding the epoxy compound to the base stock with stirring until a uniform fluid composition is obtained.

As mentioned, the base stock material which comprises at least about 50% by weight of the functional fluids of the present invention is selected from the group consisting of esters and amides of an acid of phosphorus, di- or tricarboxylic acid esters, esters of polyhydro compounds, and mixtures thereof. These base stock materials and examples thereof are described in U.S. Pat. No. 3,723,320 the subject matter of which is incorporated herein by reference.

Hydrocarbon phosphates are preferred. Phosphorus ester base stocks include trialkyl phosphates, triaryl and/or alkyl substituted aryl phosphates and mixed aryl and/or substituted arylalkyl phosphates. With respect to the alkyl groups, it is preferred to have from about 2 to about 18 carbon atoms, more preferably from about 2 to about 12 carbon atoms and with respect to the aryl and substituted aryl groups, it is preferred to have from about 6 to about 16 carbon atoms and more preferably from about 6 to about 12 carbon atoms. Typical examples of preferred phosphates are dibutylphenyl phosphate, triphenyl phosphate, tricresyl phosphate, tributyl phosphate, tri-2-ethylhexyl phosphate, trioctyl phosphate, the phosphates described in U.S. Pat. No. 3,723,315 which is incorporated herein by reference, such as di(nonylphenyl) phenyl phosphate, di(cumylphenyl) phenyl phosphate, (cumylphenyl) (nonylphenyl) phenyl phosphate, and mixtures of the above phosphates such as mixtures of tri-butyl phosphate and tricresyl phosphate, mixtures of triphenyl phosphate and 2-ethylhexyl diphenyl phosphate, mixtures of cumylphenyl diphenyl phosphate, nonylphenyl diphenyl phosphate, 2-ethylhexyl diphenyl phosphte and triphenyl phosphate. A preferred mixture contains 45 to 65% triphenyl phosphate, 25 to 45% by weight of the reaction product of 1.5 to 2 moles of nonylphenol, 0.5 to 1 mole of cumylphenol, 6 to 7 moles of phenol with 3 moles of phosphorus oxychloride and 5 to 15% of 2-ethylhexyl diphenyl phosphate. All percentages are by weight based on the total weight of the mixture. In addition to these base stock materials, the functional fluid may contain up to about 50 percent of one or more other base stock materials. Examples of these other base stock materials are given in U.S. Pat. No. 3,723,320. Although it is not permissible to employ these other base stock materials in major amounts in fluid compositions of the instant invention, they may be used singly or in combinations as a minor component of the total base stock present in amounts of less than about 50 percent by weight.

In addition to the base stock materials and the monoepoxy compounds, the fluids of the instant invention may also contain one or more base stock modifiers. As used herein, "base stock modifier" means any material which when added to the base stock effects a determinable change in the chemical or physical properties of the base stock. Examples of typical classes of such modifiers which are widely used in formulating hydraulic and other functional fluids include dyes, pour point depressants, antioxidants, antifoam agents, viscosity index improvers such as polyalkyl acrylates, polyalkyl methacrylates, polycyclic polymers, polyurethanes, polyalkylene oxides and polyesters, lubricity agents and water.

The preferred polymeric viscosity index improvers which may be employed in the compositions of this invention are the polymers of alkyl esters of unsaturated monocarboxylic acids having the formula

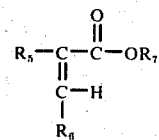

wherein $R_5$ and $R_6$ are each individually hydrogen or a $C_1$ to about $C_{10}$ alkyl group, and $R_7$ is a $C_1$ to about $C_{12}$ alkyl group. Illustration of the alkyl groups represented by $R_5$, $R_6$ and $R_7$ within their definitions as given above are for example methyl, ethyl, propyl, butyl, t-butyl, isopropyl, 2-ethylhexyl, hexyl, decyl, undecyl, dodecyl and the like. These polymers include, for example, poly(butylmethacrylates), poly(hexylmethacrylates), poly(octylacrylates), poly(dodecylacrylates) and polymers wherein the ester is a mixture of compounds obtained by esterifying the α-β unsaturated monocarboxylic acid with a mixture of monoalcohols containing from 1 to 12 carbon atoms. These and other base stock modifiers are described in U.S. Pat. No. 3,723,320.

In a preferred embodiment of the present invention the functional fluid compositions comprise at least about 50 percent by weight of a phosphate ester or mixture of phosphate esters represented by the structure

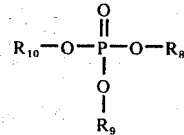

wherein $R_8$, $R_9$, and $R_{10}$ are hydrocarbon radicals selected from the group consisting of alkyl, alkoxyalkyl, aralkyl, aroxyalkyl, aryl, aroxyaryl, alkoxyaryl, alkaryl, and mxtures thereof and halogenated and alkyl-substituted members thereof having up to about 18 carbon atoms, and from about 0.1 to 10 percent by weight of an epoxy compound as hereinbefore defined. In addition to the phosphate ester and epoxy compound, these preferred fluid compositions can also contain certain additives as hereinbefore defined and can also contain minor amounts, e.g., less than about 50 percent by weight of one or more other base stock compositions as hereinbefore defined.

Particularly preferred functional fluid compositions comprise at least about 65 percent by weight of such phosphate esters and less than about 35 percent by weight of other materials including base stock and base stock modifiers, and even more preferably contain at least about 80 percent by weight of such phosphate esters and less than about 20 percent by weight of other materials. Particularly preferred phosphate esters for use in the compositions of this invention are di-alkylaryl phosphates wherein the alkyl radicals have 1 to 18 carbon atoms, e.g., dibutylphenyl phosphate, and mixtures of trialkyl phosphate and triaryl phosphate such as 88/12 tributyl phosphate/tricresyl phosphate.

The invention will now be illustrated by the following examples. All parts, proportions and percentages are by weight unless otherwise stated.

EXAMPLE I

Dibutyl-5,6-epoxy-1,4-endooxycyclohexane-2,3-dicarboxylate

A. Preparation of the dibutyl ester of 7-oxabicyclo [2.2.1] hept-5-ene-2,3-dicarboxylic anhydride.

To a suitable reaction vessel equipped with a reflux condenser and stirrer is charged 166.1 g (1.0 mole) of 7-oxa-bicyclo [2.2.1]hept-5-ene-2,3-dicarboxylic anhydride (Eastman practical grade), 280 g of n-butanol, and 1 g of p-toluene-sulfonic acid and stirred for about 28 days. During this period the temperature is kept at 50 to 55°C. The pressure is maintained at 20 to 60 Torr for about 120 hours. When it is under reduced pressure, refluxing occurs and water in the condensate steam removed.

At the end of this period, the acid number of the reaction mixture is 2.9. The mixture is then washed at room temperature once with 250 ml of water and 2 g of sodium carbonate and once with 250 ml of water. Butanol and water are stripped under reduced pressure at a maximum temperature of 57°C. The yield of the desired ester is 150 g.

B. Epoxidation of A.

To a suitable reaction vessel is charged 29.6 g (.10 mole) of Preparation A, then 22.3 g (.11 mole) of 85% assay m-chloroperbenzoic acid dissolved in 200 ml of methylene chloride is added while the reaction temperature is kept at 20°–25°C. the reaction is continued for 1–3 hours.

It is then quenched with 250 g of water, 10 g of NaHCO₃ and 1.5 g of sodium metabisulfite. This mixture is then washed with 110 g of water and 5 g of NaHCO₃ then 100 g of water. Solvent is removed by stripping under reduced pressure to final condition of 60°C. at 20 mm of Hg.

The residue is the desired epoxide.

EXAMPLE II

A functional fluid is prepared by incorporating 4% of dibutyl-5,6-epoxy-1,4-endooxycyclohexane-2,3-dicarboxylate of Example I in a base fluid comprising 94.2% dibutylphenyl phosphate; 5.1% polyalkylmethacrylate polymer V. I. improver and water 0.2%.

EXAMPLE III 2-ethylhexyl [5,6-epoxy-1,4-endooxycyclohexyl] acetate

An equimolar mixture of furan and 2-ethylhexyl vinyl acetate was heated with stirring to reflux and held at reflux or a minimum of 135°–150°C. for 4 hours. The adduct was distilled directly from the flask under vacuum. Then, 588 grams of a 27.2% by weight solution of peracetic acid in ethyl acetate was added dropwise over one hour to 266 grams of the adduct with stirring at 40°C. After an additional 2-hour period of reaction time at 40°C. with stirring, the theoretical amount of peracetic acid was consumed. The reaction mixture was distilled using ethyl benzene to facilitate the removal of acetic acid. Fractionation of the high-boiling material gave an 84% by weight yield of 2-ethylhexyl [5,6-epoxy-1,4-endooxycyclohexyl]acetate.

EXAMPLE IV 7-butoxycarbonylmethyl-6-butoxycarbonyl-3,8-dioxatricyclo [3,2.1.0$^{2,4}$] octane An equimolar mixture of furan and di-n-butylglutaconate was heated with stirring to reflux and held at reflux or a maximum of 135°–150°C. for 4 hours. The adduct was directly distilled from the flask under vacuum. Then 558 grams of a 27.2% by weight solution of peracetic acid was added dropwise over an hour to 310 grams of the adduct at 40°C. with stirring. After an additional 2-hour reaction period at 40°C. with stirring, the theoretical amount of peracetic acid was consumed. The reaction mixture was distilled using ethylbenzene to facilitate the removal of acetic acid. Fractionation of the high-boiler material gave an 80% yield of 7-butoxycarbonylmethyl-6-butoxy-carbonyl-3,8-dioxatricyclo [3,2.1.0$^{2,4}$] octane.

While this invention has been described with respect to various specific examples and embodiments, it is to be understood that the invention is not limited thereto and that it can be variously practiced within the scope of the following claims.

What is claimed is:

1. A compound represented by the following formula

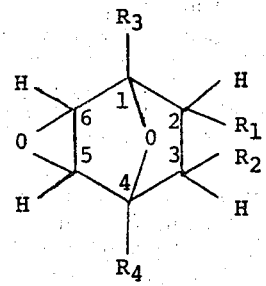

wherein $R_1$ is —$(CH_2)_{0-3}$—$C(O)OR$, —$C(O)R$, or $CH_2OR$ wherein R is an alkyl radical having from 1 to about 18 carbon atoms, $R_2$ is $R_1$, hydrogen or an alkyl radical having from 1 to 9 carbon atoms and $R_3$ and $R_4$ are individually hydrogen or an alkyl radical having from 1 to 4 carbon atoms; when $R_1$ is —$(CH_2)_0$—C(O)OR $R_2$ is not H or —$(CH_2)_0$—C(O)OR.

2. A compound according to claim 1 wherin $R_1$ is —$(CH_2)_{0-3}$—C(O)OR.

3. A compound according to claim 2 wherein R contains 1 to 9 carbon atoms.

4. A hydraulic fluid composition comprising

A. at least about 50 percent by weight of a base stock material selected from the group consisting of esters and amides of an acid of phosphorus, di- or tricarboxylic acid esters, esters of polyhydric compounds, and mixtures thereof, and B. from about 0.1 to 10 percent by weight of an epoxide compound represented by the structure

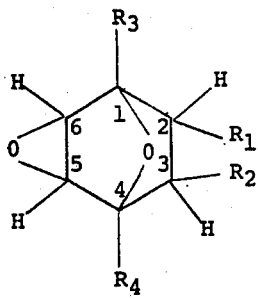

wherein $R_1$ is $-(CH_2)_{0-3}-C(O)OR$, $-C(O)R$, or $-CH_2OR$ where R is an alkyl radical having from 1 to about 18 carbon atoms, $R_2$ is $R_1$, hydrogen or an alkyl radical having from 1 to about 9 carbon atoms, and $R_3$ and $R_4$ are individually hydrogen or an alkyl radical having from 1 to about 4 carbon atoms.

5. a composition of claim 4 wherein $R_1$ is $-(CH_2)_{0-3}-C(O)OR$.

6. A compositon of claim 5 wherein the base stock material is a phosphate ester represented by the structure

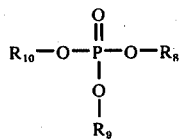

wherein $R_8$, $R_9$ and $R_{10}$ are hydrocarbon radicals selected from the group consisting of alkyl, alkoxyalkyl, aralkyl, aroxyalkyl, aryl, aroxyaryl, alkoxyaryl, alkaryl, and mixtures thereof and halogenated and alkyl-substituted members thereof having up to about 18 carbon atoms.

7. A composition of claim 6 wherein $R_9$ and $R_{10}$ are $C_{1-18}$ alkyl radicals and $R_8$ is a $C_6-C_{18}$ aryl radical.

8. A composition of claim 6 wherein the phosphate ester is dibutylphenylphosphate.

9. A composition of claim 8 wherein the epoxide compound is $C_{1-12}$ alkyl-1,4-endooxycyclohexane-2-carboxylate.

10. A composition of claim 6 wherein the phosphate ester is a mixture of tributyl phosphate and triaryl phosphate.

11. A composition of claim 10 wherein the epoxide compound is $C_{1-12}$ alkyl-5,6-epoxy-1,4-endooxycyclohexane-2-carboxylate.

12. A functional fluid composition comprising a composition of claim 6 and from about 2 to 20 percent by weight of a viscosity index improver which is a polymer of an ester having the structure

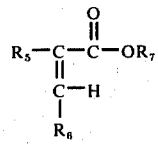

wherein $R_5$ and $R_6$ are each individually hydrogen or a $C_1$ to about $C_{10}$ alkyl group, and $R_7$ is a $C_1$ to about $C_{12}$ alkyl group.

13. A functional fluid composition comprising a composition of claim 6 and from about 2 to 20 percent by weight of a viscosity index improver which is a polymer of an alkylene oxide having a polymeric molecular weight of from about 1,500 to 4,500.

14. In a method of operating a hydraulic pressure device wherein a displacing force is transmitted to a displaceable member by means of a hydraulic fluid, the improvement which comprises employing as said fluid a composition of claim 4.

15. In a method of operating a hydraulic pressure device wherein a displacing force is transmitted to a displaceable member by means of a hydraulic fluid, the improvement which comprises employing as said fluid a composition of claim 12.

* * * * *

UNITED STATES PATENT OFFICE
CERTIFICATE OF CORRECTION

PATENT NO. : 3,969,254
DATED : July 13, 1976
INVENTOR(S) : John F. Herber et al

It is certified that error appears in the above-identified patent and that said Letters Patent are hereby corrected as shown below:

Column 1, line 30, "In order the control the degree of acid buildup during" should be --- In order to control the degree of acid buildup during ---.

Column 8, line 22, "tricyclo [3,2.10$^{2.4}$] octane" should be --- tricyclo [3,2.1.0$^{2.4}$] octane ---.

Column 9, line 29, first word, "a" should be --- A ---.

Column 10, Claim 9, line 2, "compound is $C_{1-12}$ alkyl-1,4-endooxycyclohexane-2-" should be --- compound is $C_{1-12}$ alkyl-5,6-epoxy-1,4-endooxycyclohexane-2- ---.

Signed and Sealed this

Nineteenth Day of October 1976

[SEAL]

Attest:

RUTH C. MASON
Attesting Officer

C. MARSHALL DANN
Commissioner of Patents and Trademarks